United States Patent

Hansen

[11] Patent Number: 5,316,554
[45] Date of Patent: May 31, 1994

[54] METHOD FOR PROCESSING CRYSTALLINE AMMONIUM CARBAMATE

[76] Inventor: Charles N. Hansen, 1448 South 1700, Salt Lake City, Utah 84108-2602

[21] Appl. No.: 102,991

[22] Filed: Jul. 28, 1993

Related U.S. Application Data

[63] Continuation-in-part of Ser. No. 892,924, Jun. 3, 1992, abandoned.

[51] Int. Cl.$^5$ .................. B01D 9/00; C01B 3/00; C07C 273/00
[52] U.S. Cl. .................. 23/300; 23/295 R; 23/313 R; 23/313 P; 564/66; 564/70; 423/415.1; 423/420
[58] Field of Search .................. 423/420, 437, 415.1, 423/420; 564/65, 66, 67, 68, 69, 70, 71, 72; 23/295, 313 P, 300, 313 R; 567/555

[56] References Cited

U.S. PATENT DOCUMENTS

| | | | |
|---|---|---|---|
| 1,909,757 | 5/1933 | Coxon | 423/420 |
| 3,310,367 | 3/1967 | Mavrovic | 423/420 |
| 3,940,440 | 2/1976 | Mavrovic | 564/71 |
| 3,944,605 | 3/1976 | Inoue et al. | 564/71 |
| 4,088,684 | 5/1978 | Mavrovic | 564/71 |
| 4,169,499 | 10/1979 | Le Fois | 165/1 |
| 4,231,961 | 11/1980 | Konoki et al. | 564/65 |
| 4,539,077 | 9/1985 | Jonckers et al. | 564/69 |
| 4,567,294 | 1/1986 | Dressel et al. | 562/555 |
| 4,587,358 | 5/1986 | Blouin | 564/3 |
| 4,652,678 | 3/1987 | Douwes | 423/437 |
| 4,698,173 | 10/1987 | Hansen | 252/70 |
| 4,988,491 | 1/1991 | Van Dijk et al. | 564/60 |

FOREIGN PATENT DOCUMENTS 3346719 7/1985 Fed. Rep. of Germany ...... 423/420

OTHER PUBLICATIONS

Mars Mineral Leaflet MMC-202; Research Test Options Possible Test Options for Pelletizing of Fine Materials.
Impact Type Pulverizers, Pulva Corporation.
Science/Technology Concentrate, May 26, 1986, C & EN.
A Study of Anticaking Treatments for Urea, by Geo. M. Blouin and A. W. Allen, Tennessee Valley Authority, Sep. 9–12, 1985.
G. G. Choudhry et al., *Humic Substances*, 1984 pp. 5–11 and 118–123.

*Primary Examiner*—Gary P. Straub
*Attorney, Agent, or Firm*—Dowell & Dowell

[57] ABSTRACT

Ammonium carbamate, in solution with urea, water and ammonia and under high temperature and pressure is cooled to below its crystallization temperature while being subjected to an elevated pressure. The crystallized substance formed is then dried, crushed, and pelletized with the aid of a binding agent to produce pellets having substantial strength and stability, and having particular utility as a deicer for roadways.

26 Claims, 1 Drawing Sheet

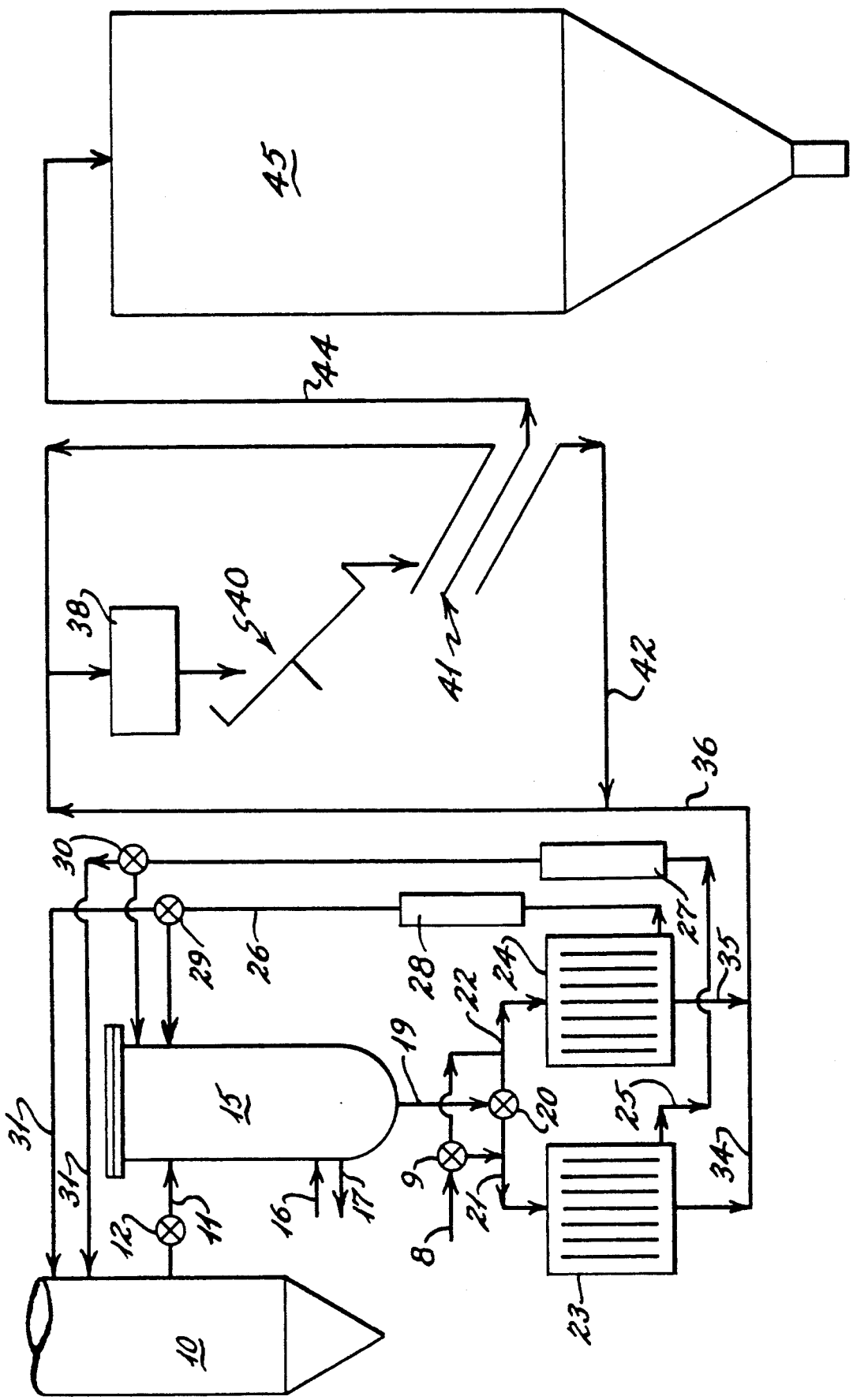

METHOD FOR PROCESSING CRYSTALLINE AMMONIUM CARBAMATE

CROSS-REFERENCE TO RELATED APPLICATIONS

This application is a continuation-in-part application of pending U.S. patent application Ser. No. 07/892,924, filed Jun. 3, 1992 abandoned.

BACKGROUND OF THE INVENTION

Ammonium carbamate is not an available commercial product. It occurs as an intermediate product in the production of urea, and apparently it has never been separated and removed from urea plants due to the lack of any market.

A patent for using ammonium carbamate as a deicer was issued to Hansen as U.S. Pat. No. 4,698,173 on Oct. 6, 1987. This deicer does not corrode steel or aluminum, and instead of being toxic to plant life as are commonly used highway deicers, the contained nitrogen actually promotes plant growth. Tests at the Utah Department of Transportation also demonstrated that an ammonium carbamate deicer dramatically reduced the freezing damage to concrete. In 1976, the Environmental Protection Agency estimated that the use of nine million tons of salt per year as a deicer, costs the public about five billion dollars per year at a cost of about $555 per ton. With the potential money to be saved by using a deicer of moderate price and which does not damage the environment, and with a potential market of about nine million tons per year, it became evident to the present inventor that there would be numerous benefits if the ammonium carbamate could be commercially produced. Furthermore, urea production plants are a logical available source of ammonium carbamate.

The process of removing ammonium carbamate from a urea plant presented several problems, however. One of the principle problems was that it existed in the urea production plant under high temperature and pressure. A method had to be devised for removing the ammonium carbamate from the water and ammonia solvents it is in solution with and converting it to a useable state, which is crystalline in this case.

A second problem to be solved was to devise a method of making the ammonium carbamate crystals into granules or pellets which can be distributed on roads. In attempting to solve this problem, the present inventor discovered that the crystals produced contained too much moisture to be pelletized or granulated and so a method had to be devised to remove the water from the crystals. In addition, after learning how to remove the water from the crystals, a method of granulating or pelletizing the crystals had to be devised. Finally, a binder that would hold the pellets together, as well as a technique to keep the pellets stable for subsequent use, were also needed.

PRODUCTION OF AMMONIUM CARBAMATE

Two molal volumes of ammonia can be reacted at high pressure with one molal volume of carbon dioxide to produce ammonium carbamate in an autoclave reactor in a urea production plant. A separate facility for this purpose alone could be built for use according to the present invention, but such facility would require substantial financial investment. In an existing urea production plant, the ammonium carbamate is circulated through conversion towers, where about one-half of the ammonium carbamate is converted into urea and water. The remaining ammonium carbamate, along with the water released and excess ammonia, are pumped back against high pressure into the reactor. Such remaining ammonium carbamate may then be removed from the reactor for use in accordance with the present invention.

Thus, a urea production plant may be used to produce approximately twice as much useable product; that is, for every 100 pounds of urea previously produced, the plant would now produce approximately 100 pounds of urea and approximately 100 pounds of ammonium carbamate. The enhancement of production in a urea plant and the relatively inexpensive potential source of ammonium carbamate provided considerable incentives for the present inventor to learn how to recover ammonium carbamate from a urea production plant and then to produce a product from the ammonium carbamate which would be suitable for use as a deicer.

CRYSTALLIZING AMMONIUM CARBAMATE FROM RECYCLED SOLUTIONS

In the early part of the present inventor's research for a method of producing ammonium carbamate from a urea plant, it was necessary to determine the condition and composition of the chemicals which were being returned to the reactor. The returned ammonium carbamate and a small amount of urea were found to be dissolved in a solution of water and ammonia.

An analysis of a solution used in one test in which 1368 grams of solution were present in the crystallization chamber gave the following composition: 41.79% $NH_3$, 27.19% $CO_2$, 3.87% urea and 27.15% $H_2O$.

Because ammonium carbamate is produced from two moles of ammonia and one mole of carbon dioxide, and there is an excess of ammonia in this composition, the contained ammonium carbamate is calculated from the content of carbon dioxide as follows:

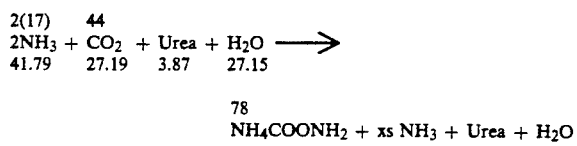

| Calculated Composition of the Absorber Bottoms Solution | | |
|---|---|---|
| | Percent | Grams |
| (27.19/44) (78) | = 48.21 $NH_4COONH_2$ | 659.5 |
| 41.79 − (27.19/44) (34) | = 20.77 xs $NH_3$ | 284.2 |
| | = 3.87 Urea | 52.9 |
| | = 27.15 $H_2O$ | 371.4 |
| TOTAL | 100.00 | 1368.0 |

With reference to table V-4 on pages 258–259 of the 1967 edition of "Urea Its Properties and Manufacture" by George Tseiyu Chao, it was determined that this solution would become super saturated during cooling and crystals would form. It was estimated, from this table, that in a crystallization chamber containing cooling water at 10° C., the temperature of the ammonium carbamate solution could be lowered to between 15° C.-20° C. A test was then set up from which the above composition of the ammonium carbamate solution was taken and the temperature of the solution being crystallized was lowered to 16.7° C.

In this test, the 1368 grams of absorber bottoms liquid was placed in the crystallization chamber to produce 960 grams of crystals having the following composition:

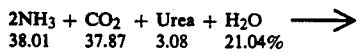
2NH$_3$ + CO$_2$ + Urea + H$_2$O ⟶
38.01    37.87    3.08    21.04%

NH$_4$COONH$_2$ + xs NH$_3$ + Urea + H$_2$O

| Calculated Composition of the Crystals Formed | | |
|---|---|---|
| | Percent | Grams |
| (37.87/44) (78) | = 67.13 NH$_4$COONH$_2$ | 644.4 |
| 38.01 − (37.87/44) (34) | = 8.75 NH$_3$ | 84.0 |
| | = 3.08 Urea | 29.6 |
| | = 21.04 H$_2$O | 202.0 |
| TOTAL | 100.00 | 960.0 |

| Recovery of Chemicals Into the Crystals | | |
|---|---|---|
| Recovery of ammonium carbamate | 644.4/659.5 | 97.7% |
| Recovery of ammonia | 84.0/284.2 | 29.6% |
| Recovery of urea | 29.6/52.9 | 56.0% |
| Recovery of water | 202.0/371.4 | 54.4% |

EXPECTED RECOVERY OF AMMONIUM CARBAMATE INTO THE CRYSTALS

The following table gives the composition of the bottoms liquid with and without the contained urea.

| | With Urea (%) | Without Urea (%) |
|---|---|---|
| NH$_4$COONH$_2$ | 48.21 | 50.13 |
| NH$_3$ | 20.77 | 21.62 |
| Urea | 3.87 | — |
| H$_2$O | 27.15 | 28.24 |
| TOTAL | 100.00 | 100.00 |

From the table on pages 258–159 of the aforementioned book by Chao, it was expected that at a temperature of 16.7° C., the crystals which were formed from the above solution would have been in equilibrium with a solution having the following composition:

| NH$_4$COONH$_2$ | 30.0% |
|---|---|
| NH$_3$ | 30.0% |
| H$_2$O | 40.0% |
| TOTAL | 100.0% |

Such a crystallization process would produce the following expected recovery of the ammonium carbamate, wherein:
Weight of original solution = 100 g,
weight of solution in equilibrium with crystals = X; and
weight of crystals formed = (100−X).

Thus, 100×0.5013−0.30X (100−X) = weight of crystals formed, and X=71.24 g. Accordingly, the weight of the crystals equals 100−71.24=28.76 g, and the expected recovery was only 28.76/50.13=57.4%.

After measuring this unexpected increase in the actual recovery of the crystals as compared with the expected recovery, it was determined that additional tests should be run. After running these additional tests and studying their results, it became quite apparent that there are two main factors which are important in determining the percentage of ammonium carbamate which can be crystallized from the bottoms liquid solution: (1) a low final temperature and (2) a high pressure. The present invention comprises the discovery of the importance of maintaining a high pressure during the crystallization process.

BRIEF DESCRIPTION OF THE DRAWINGS

In the accompanying drawing:
FIG. 1 is a schematic drawing of a pilot plant for producing ammonium carbamate in accordance with the present invention.

DETAILED DESCRIPTION OF THE PREFERRED EMBODIMENT

Crystallizing Ammonium Carbamate

It was determined that an appropriate place to secure a sample of the solution being recycled in the urea plant was from the bottom of a first absorber. At this location the bottoms liquid is at a pressure of about 225 psig and a temperature of about 180° F. (about 82° C.).

The liquid sample was filled into an aluminum crystallization chamber which was formed from an eleven inch length piece of four inch, schedule 80 aluminum pipe, which was closed on the bottom with a four inch schedule 80 aluminum weld cap and on the top with two aluminum flanges. One of these flanges was welded to the pipe and then bolted to the top flange with eight one-half inch bolts. The four inch pipe was surrounded with a nine inch length piece of five inch, schedule 40 aluminum pipe, closed at both ends to form a cooling chamber. The line through which the crystallization chamber was filled and from which the gases were exhausted, entered through the side of the chamber at about two inches from the top. The openings for the pressure gauge and a thermal well for measuring temperature were defined by the top flange. Nine baffles were placed between the outside and inside aluminum pipes for the purpose of circulating the cooling water from the top to bottom as it cooled the contained bottoms liquid. The openings for the cooled water were through two one-fourth inch pipes in the side of the five inch aluminum pipe.

Before filling the crystallization chamber, the tare weight of the chamber was determined and recorded. As the crystallization chamber was filled, the pressure and temperature of the filled chamber were recorded. The gross weight of the filled chamber was then determined and recorded and the cooling process was started. The temperature and pressure of the contained solution were recorded at one minute intervals as the solution cooled. Except for the early tests, which were stopped at 16.7° C., the crystallization tests were stopped at one of three temperatures; namely, 30° C., 20° C. and 15.7° C.

At the conclusion of each test, the gases were exhausted and the crystallization chamber was then weighed. The chamber was then opened, the contained clear solution was decanted therefrom, and the chamber was reweighed. The contained crystals were then sampled and analyzed.

After it became apparent to the present inventor that it was important to maintain a high pressure in order to increase the recovery of crystals from the bottoms liquid, the recorded information was examined and the pressure, at the highest temperature at which the tests were concluded, 30° C., was noted. Following are the results of those tests.

EXAMPLE E14A1

| | |
|---|---|
| Crystallization chamber filled at Pressure at 30° C. | 100 psi |
| | 39 psi |
| Temperature at completion of test | 30° C. |
| Weight of absorber bottoms liquid taken into chamber | 318 g |
| Weight of crystals recovered | 114 g |
| Weight of filtrate recovered | 86 g |
| Weight of gases and liquid vented and lost | 118 g |

Composition of Products (%)

| Name of Product | $NH_4COONH_2$ | xs $NH_3$ | Urea | Water |
|---|---|---|---|---|
| Absorber Bottoms Liquid | 48.36 | 22.01 | 3.50 | 26.13 |
| Crystals | 38.70 | 19.20 | 2.18 | 39.96 |
| Percent Recovery | | | | |
| Percent Into Crystals | 28.7 | 31.2 | 22.3 | 54.8 |

EXAMPLE E15A1

| | |
|---|---|
| Crystallization chamber filled at Pressure at 30° C. | 100 psi |
| | 51 psi |
| Temperature at completion of test | 15.7° C. |
| Weight of absorber bottoms liquid taken into chamber | 485 g |
| Weight of crystals recovered | 249 g |
| Weight of filtrate recovered | 126 g |
| Weight of gases and liquid vented and lost | 110 g |

Composition of Products (%)

| Name of Product | $NH_4COONH_2$ | xs $NH_3$ | Urea | Water |
|---|---|---|---|---|
| Absorber Bottoms Liquid | 45.77 | 22.08 | 4.44 | 27.71 |
| Crystals | 75.64 | 2.47 | 2.83 | 19.06 |
| Percent Recovery | | | | |
| Percent Into Crystals | 84.7 | 5.7 | 32.7 | 35.3 |

EXAMPLE E15A2

| | |
|---|---|
| Crystallization chamber filled at Pressure at 30° C. | 160 psi |
| | 61 psi |
| Temperature at finish of test | 20° C. |
| Weight of absorber bottoms liquid taken into chamber | 1195 g |
| Weight of crystals recovered | 700 g |
| Weight of filtrate recovered | 300 g |
| Weight of gases and liquid vented and lost | 195 g |

Composition of Products (%)

| Name of Product | $NH_4COONH_2$ | xs $NH_3$ | Urea | Water |
|---|---|---|---|---|
| Absorber Bottoms Liquid | 46.67 | 20.22 | 4.64 | 28.46 |
| Crystals | 74.92 | 3.93 | 2.78 | 18.37 |
| Percent Recovery | | | | |
| Percent Into Crystals | 94.0 | 11.4 | 35.2 | 37.8 |

EXAMPLE E16A1

| | |
|---|---|
| Crystallization chamber filled at Pressure at 30° C. | 160 psi |
| | 74 psi |
| Temperature at completion of test | 30° C. |
| Weight of absorber bottoms liquid taken into chamber | 1433 g |
| Weight of crystals recovered | 803 g |
| Weight of filtrate recovered | 365 g |
| Weight of gases and liquid vented and lost | 265 g |

Composition of Products (%)

| Name of Product | $NH_4COONH_2$ | xs $NH_3$ | Urea | Water |
|---|---|---|---|---|
| Absorber Bottoms Liquid | 46.36 | 21.78 | 3.83 | 28.03 |
| Crystals | 72.50 | 4.75 | 2.40 | 20.35 |
| Percent Recovery | | | | |
| Percent Into Crystals | 87.6 | 12.2 | 35.2 | 40.7 |

EXAMPLE E16A2

| | |
|---|---|
| Crystallization chamber filled at Pressure at 30° C. | 210 psi |
| | 84 psi |
| Temperature at completion of test | 20° C. |
| Weight of absorber bottoms liquid taken into chamber | 1929 g |
| Weight of crystals recovered | 1158 g |
| Weight of filtrate recovered | 437 g |
| Weight of gases and liquid vented and lost | 334 g |

Composition of Products (%)

| Name of Product | $NH_4COONH_2$ | xs $NH_3$ | Urea | Water |
|---|---|---|---|---|
| Absorber Bottoms Liquid | 47.12 | 21.79 | 4.06 | 27.03 |
| Crystals | 75.98 | 0.00 | 2.48 | 21.54 |
| Percent Recovery | | | | |
| Percent Into Crystals | 96.8 | 00.0 | 36.7 | 47.8 |

EXAMPLE E17A1

| | |
|---|---|
| Crystallization chamber filled at Pressure at 30° C. | 215 psi |
| | 46 psi |
| Temperature at completion of test | 15.7° C. |
| Weight of absorber bottoms liquid taken into chamber | 2069 g |
| Weight of crystals recovered | 1199 g |
| Weight of filtrate recovered | 442 g |
| Weight of gases and liquid vented and lost | 428 g |

Composition of Products (%)

| Name of Product | $NH_4COONH_2$ | xs $NH_3$ | Urea | Water |
|---|---|---|---|---|
| Absorber Bottoms Liquid | 49.83 | 21.09 | 4.26 | 24.82 |
| Crystals | 71.33 | 6.83 | 2.55 | 19.29 |
| Percent Recovery | | | | |
| Percent Into Crystals | 82.9 | 18.8 | 34.7 | 45.0 |

EXAMPLE E17A2

| | |
|---|---|
| Crystallization chamber filled at Pressure at 30° C. | 215 psi |
| | 72 psi |
| Temperature at completion of test | 30° C. |
| Weight of absorber bottoms liquid taken into chamber | 1857 g |
| Weight of crystals recovered | 978 g |
| Weight of filtrate recovered | 610 g |
| Weight of gases and liquid vented and lost | 269 g |

Composition of Products (%)

| Name of Product | $NH_4COONH_2$ | xs $NH_3$ | Urea | Water |
|---|---|---|---|---|
| Absorber Bottoms Liquid | 44.46 | 22.37 | 5.03 | 28.14 |
| Crystals | 76.58 | 4.01 | 2.47 | 16.94 |
| Percent Recovery | | | | |
| Percent Into Crystals | 90.7 | 9.4 | 42.0 | 31.7 |

EXAMPLE D2A1

| | |
|---|---|
| Crystallization chamber filled at Pressure at 30° C. | 200 psi |
| | 62 psi |
| Temperature at completion of test | 16.7° C. |
| Weight of absorber bottoms liquid taken into chamber | 1368 g |
| Weight of crystals recovered | 960 g |
| Weight of filtrate recovered | 408 g |

Composition of Products (%)

| Name of Product | $NH_4COONH_2$ | xs $NH_3$ | Urea | Water |
|---|---|---|---|---|
| Absorber Bottoms Liquid | 48.21 | 20.77 | 3.87 | 27.15 |
| Crystals | 67.13 | 8.75 | 3.08 | 21.04 |
| Percent Recovery | | | | |
| Percent Into Crystals | 97.7 | 29.6 | 56.0 | 54.4 |

DISCUSSION OF THE TEST RESULTS

As expected, the percentage of ammonium carbamate crystals recovered from the solution of ammonium carbamate in a water and ammonia solvent was a function of the temperature to which the solution was cooled during the crystallization process. Unexpectedly, it was also discovered that if the ammonium carbamate solution was maintained under pressure as the crystals were being formed, the percentage of ammonium carbamate recovered into the crystals was also a function of pressure. More particularly, the higher the pressure that was maintained in the crystallization chamber, the higher was the percentage of ammonium carbamate recovered into the crystals.

The following table compares the per cent recovery at the final temperatures of 30° C., 20° C. and 15.7° C. to the recovery made at the various pressures which were maintained until the temperature was reduced to the highest final temperature of crystallization, 30° C.

| Test No. | Pressure Maintained To 30° C. | Percent Recovery at Temperature | | |
|---|---|---|---|---|
| | | 30° C. | 20° C. | 15.7° C. |
| E16A2 | 84 psi | | 96.8 | |
| E16A1 | 74 psi | 87.6 | | |
| E17A2 | 72 psi | 90.7 | | |
| D2A1 | 62 psi | | | 97.7 |
| E15A2 | 61 psi | | 94.0 | |
| E15A1 | 51 psi | | | 84.7 |
| E17A1 | 46 psi | | | 82.9 |
| E14A1 | 39 psi | 28.7 | | |

The tests which were completed at 30° C. demonstrated that as the pressure was increased from 39 psi to 72 psi and to 74 psi, the recovery increased from 28.7% to an average of about 89%. The difference in test results between the ending pressures of 61 psi and 84 psi for a temperature of 20° C. was not as great, but in both cases the per cent recovery was excellent. At 15.7° C., the difference between the 82.9% recovery at 46 psi and the 97.7% recovery at 62 psi was substantial.

These test results demonstrated that it is advantageous to maintain a high pressure during the crystallization process. Based on the results, this pressure should be above approximately 50 psig. Such pressure can be maintained by pressurizing the vessel with the liquid that is being crystallized or with any gas, such as ammonia or nitrogen, that is compatible with the ammonia and water solvents from which the ammonium carbamate crystallizes.

REMOVING WATER FROM AMMONIUM CARBAMATE CRYSTALS

Ammonium carbamate, like many other chemicals, has a vapor pressure which is a function of its temperature. According to Chao at page 299, the dissociation pressure of solid ammonium carbamate in the temperature range of 283° K to 355° K (10° C. to 82° C.) can be calculated from the equation, Log $P = -2741.9/T + 11.1448$. To illustrate how the dissociation pressure changes with temperature, the pressures were calculated at the following temperatures. At temperatures below 10° C., the pressure are probably estimates:

| Temperature | | | Pressure | | |
|---|---|---|---|---|---|
| °F. | °C. | °K. | Log P mm Hg | P mm Hg | P psig |
| 32.0 | 0.0 | 273 | 1.1012 | 12.62 | 0.244 |
| 40.0 | 4.4 | 277 | 1.2621 | 18.29 | 0.353 |
| 50.0 | 10.0 | 283 | 1.4561 | 28.58 | 0.553 |
| 60.0 | 15.6 | 288.6 | 1.6426 | 43.92 | 0.849 |
| 70.0 | 21.1 | 294.1 | 1.8221 | 66.39 | 1.284 |
| 80.0 | 26.7 | 299.7 | 1.9950 | 98.85 | 1.912 |
| 90.0 | 32.2 | 305.2 | 2.1615 | 145.05 | 2.806 |
| 100.0 | 37.8 | 310.7 | 2.3221 | 209.90 | 4.061 |
| 140.0 | 60.0 | 333 | 2.9109 | 814.5 | 15.75 |

An attempt was made to dry the crystals by heating them, but by comparing the vapor pressure of ammonium carbamate at 37.8° C. with the vapor pressure of water at this same temperature, that is 209.9 mm Hg versus 49.157 mm Hg, it became apparent that the ammonium carbamate would evaporate much faster than the water.

A chamber for filtering the ammonium carbamate crystals and then washing them with liquid ammonia was designed and manufactured. The chamber was constructed from an 18 inch length piece of 8 inch, schedule 40 aluminum pipe. To each end of the aluminum pipe was welded an 8 inch aluminum flange and the chamber was then closed with a blind 8 inch flange at each end. A filtering plate was welded into the interior of the chamber at a location 8 inches from the bottom of the chamber and 10 inches from the top. The filter plate contained 396 holes, each having a 1/16 inch diameter. The holes were drilled in concentric ring patterns about a center hole. The rings formed by the holes were about ⅜ of an inch apart. The outer ring contained 66 holes and each successively smaller ring contained six less holes than the previous ring, continuing to the center ring which contained 6 holes. A 20 cm filter paper was placed on this filter plate before the filtering and washing operation was conducted.

Into the top flange, about one inch from the inside wall of the chamber, a ¼ inch hole was tapped for receiving a pressure gauge. The liquid ammonia for washing the ammonium carbamate crystals was circulated through a ⅜ inch pipe and a spray head which formed a solid cone-shaped spray. The spray head was placed at a height above the filter cake that allowed uniform washing of the filter cake.

A ⅜ inch hole was tapped in the center of the bottom flange and was used as the drain line for the chamber. About one inch from the inside edge of the chamber, a ¼ inch hole was tapped in the bottom flange and a standpipe was placed inside the chamber. This standpipe and attached pipe to the outside were used to control the pressure in the base of the chamber. All pipes which led into or out of the chamber were closed with valves and a pressure gage was coupled to the standpipe line.

The following procedure was followed in washing the moisture from the ammonium carbamate crystals. After decanting the liquid from the crystals in the crystallization chamber, the crystals were transferred to the filtration and washing chamber. The crystals were spread out evenly and the wet crystals were packed onto the filter paper and filtered for ten minutes by applying a vacuum through the standpipe line of the chamber and closing the drain line. After filtering the crystals, the valve on the standpipe line was closed and the drain line valve was opened and the filtered liquid was allowed to drain. The cover of the filtration and washing chamber was closed, and prior to washing the crystals with ammonia, the pressure of the chamber was increased with nitrogen gas to about 40 psig.

As the crystals were being washed with ammonia, the opening of the drain valve was carefully regulated to maintain a pressure in the washing chamber at above 20 psig. Whenever the drain valve began to plug, the opening of the valve was washed with water.

After the last ammonia cylinder had been used to wash the crystals, the drain valve was opened to reduce the pressure in the chamber. When the pressure had been reduced, the chamber and contained filter cake were aerated by running compressed air into the ammonia line and out through the drain line.

The chamber was then opened and the crystals were removed and weighed. The crystals were spread over a shallow pan, and any lumps present were crushed and the contained gases were allowed to escape. The crystals were sampled and analyzed for water content.

For each test, the test number, weight of the wet crystals, and the number of washes were recorded. Following is a summary of the test results:

Summary of Filtering and Washing Results

| Examp. No. | Weight of Wet Crystals (g) | Number of Washes | Washes Per 1000 g of Wet Crystals | % Water in Washed Crystals | Remarks |
|---|---|---|---|---|---|
| K4B1 | 1180 | 9 | 7.6 | 1.8 | |
| K4B2 | 1403 | 8 | 5.7 | 0.76 | |
| K5B1 | 1480 | 8 | 5.4 | 1.4 | |
| K6B1 | 1700 | 10 | 5.8 | 4.6 | pressure below 10 psi |
| K6B2 | 1390 | 9 | 6.5 | 0.32 | |
| K7B1 | 1345 | 7 | 5.0 | 1.3 | |

Each of the pressure cylinders used in the washes had a capacity of 500 ml and contained about 400 ml of liquid ammonia.

An important aspect of the present invention is to wash the crystals with liquid ammonia so as to reduce the percentage of water contained therein. During the washing of crystals with liquid ammonia, it is important to maintain a sufficiently high pressure in the filtration and washing chamber to prevent the ammonia from flashing to a gas before it passes through the filter cake.

When the pressure in the washing chamber was allowed to drop below about 20 psig, the liquid ammonia entering the chamber flashed to a gas and instead of washing the crystals with a liquid, they were washed with a gas which was less effective in removing water from the crystals. Any ammonia which flashed to a gas in the washing chamber possibly lowered the temperature of the chamber so that at 20 psig, the ammonia sprayed therein remained sufficiently liquid to wash the water from the ammonium carbamate crystals.

Example No. K6B1 demonstrates how less effective washing with a gas is as compared to washing with liquid ammonia. Disregarding Test No. K6B1, an average of 6.04 washes produced an average moisture content in the crystals of 1.12%. On this basis, it took about 6.8 washes to lower the moisture content of 1000 grams of wet crystals to a level of 1%.

CRUSHING AMMONIUM CARBAMATE CRYSTALS AND PRODUCING PELLETS THEREFROM

Before the present inventor learned that the crystals contained too much water to produce granules or pellets, many methods of granulation were attempted. The crystals were heated in the laboratory over a steam bath to their softening point, and then allowed to cool while being stirred. Using this method, granules of about ⅜ inch diameter were produced. These granules, however, did not retain their strength.

Two different devices for compacting the crystals were designed. Using these devices, the crystals were formed into rather strong cylindrical pellets, but it was discovered that after long standing the pellets lost their structural strength.

Crystals were next submitted to a commercial pellet mill to be tested for making pellets with its equipment, but in the pelletizing process, the crystals became so hot that they fumed.

Further experiments included placing crystals in the bottom of a beaker which was tilted and rotated. These experiments revealed that a pan granulator would be a good device for producing pellets from the ammonium carbamate crystals. Accordingly, arrangements were made with another company to conduct a pan granulation test.

PELLETIZATION TESTING

Using both ammonium and calcium lignosulfonate as binders, tests were conducted which produced unsuccessful results. It was learned from these tests that the lignosulfonates were poor binders for this system and that the crystals needed to be passed through a screen before being granulated.

The present inventor conducted tests to illustrate the discovery that humic acid is an effective binder for forming ammonium carbamate into pellets. Literature from SURFACTANT TECHNOLOGIES CORPORATION describes its product, Surtech L-101, as being a lignite and being composed of about 30% hydrophobic clay, 30% humic acid and the remainder being water plus the requisite organics (wax). Solutions comprising L-101 were made by adding 5%, 10% and 20%, respectively, of pulverized L-101 to aqua ammonia. Aqua ammonia was used as the solvent because it dissolves humic acid and the contained ammonia, and prevents the water from hydrolyzing the ammonium carbamate to ammonium carbonate. In making these solutions, only the humic acid was soluble. The undissolved clay and organics formed a deposit in the bottom of the container.

The 5% solution of L-101 contained the following: $(0.05 \times 30)/(0.05 \times 30 + 95) = 1.55\%$ humic acid dissolved in an aqua ammonia solution.

The 10% solution contained: $(0.1 \times 30)/(0.1 \times 30 + 90) = 3.2\%$ humic acid dissolved in an aqua ammonia solution.

The 20% solution contained: $(0.2 \times 30)/(0.2 \times 30 + 80) = 7.0\%$ humic acid dissolved in aqua ammonia.

It was determined that the 10% solution represented about the limit of solubility of the humic acid in aqua ammonia and accordingly the subsequent test work was performed using a 10% solution of Surtech L-101.

Using an eyedropper, and weighing 100 drops of the 10% solution, it was determined that after the addition of the first 20 drops, each 20 drop addition of solution increased the weight of the solution by 0.8782, 0.9384, 0.9308 and 0.9680 grams, or an average of 0.92885 grams per 20 drops, or an average of 0.0464 grams per drop.

One drop of this solution was then added to the following weights of pulverized ammonium carbamate crystals and each wetted mass was rolled into a pellet with the following results:

| Ammonium Carbamate Bonded With a Solution of Humic Acid in Aqua Ammonia | | | |
|---|---|---|---|
| EXAMPLE NO. | Grams of Ammonium Carbamate | Percent Bonding Solution | Remarks |
| F16D1 | 0.3500 | 11.7 | Pellet was too wet and took about 10 minutes to set up |
| F16D2 | 0.3850 | 10.8 | Pellet was still too wet and took about 5 minutes to set up |
| F16D3 | 0.4240 | 9.9 | Pellet was somewhat wet and took about 5 minutes to set up |
| F16D4 | 0.4660 | 9.1 | Pellet was less wet and took about 4½ minutes to set up |
| F16D5 | 0.513 | 8.3 | Pellet was less wet and took about 4½ minutes to set up |
| F16D6 | 0.564 | 7.6 | Pellet was somewhat dry and took about 4½ minutes to set up |
| F16D7 | 0.620 | 7.0 | Pellet was dry and took about 4½ minutes to set up |
| F16D8 | 0.682 | 6.4 | There was not enough solution to bond the crystals into a pellet |

Based on these results, a pellet containing approximately 8% of the bonding solution has the optimum characteristics. At about 3% humic acid in the bonding solution, the pellet contained approximately $0.03 \times 8\% = 0.24\%$ humic acid. From the above data, the humic acid is preferably present at from between 0.21% to 0.35%, and, more preferably, about 0.24%.

The present inventor also conducted tests to illustrate the discovery that a soy based protein bonds ammonium carbamate into pellets. This protein from SURFACTANT TECHNOLOGIES CORPORATION is identified as Surtech P-827 and is described as a 100% active modified polypeptide. It is, however, according to later information, a soy based protein with a molecular weight of 150,000 to 200,000. The manufacturer's literature indicates that a 5% or more solution of Surtech P-287 in water plus enough ammonia to raise the pH to about 9.5 to 10 can be made. In an aqua ammonia solution that would not hydrate the ammonium carbamate to ammonium carbonate, a 5% of the Surtech P-827 was determined to be about the maximum amount that could be put into solution. Accordingly, a 5% solution of Surtech P-827 was made up and 110 drops of the solution was weighed at 20 drop intervals. The increase in weight with each 20 drops was as follows: $0.6049 + 0.6046 + 0.6518 + 0.6186 + 0.6442 + 0.6698 = 3.7939$ grams. The average weight of each 20 drops was 0.6323, or an average weight per drop of 0.0316 grams.

One drop of the 5% bonding solution was then added to various weights of pulverized ammonium carbamate and each wetted mass was then rolled into a ball to form pellets and the following results were obtained:

| Ammonium Carbamate Bonded With a Solution of a Soy Based Protein in Aqua Ammonia | | | |
|---|---|---|---|
| EXAMPLE NO. | Grams of Ammonium Carbamate | Percent Bonding Solution | Remarks |
| F21D1 | 0.3630 | 8.0 | Pellet was not wet and set up about 5 minutes |
| F21D2 | 0.3990 | 7.3 | Not sufficient bonding solution to form a pellet |
| F21D3 | 0.3300 | 8.7 | Pellet was not wet and took less than 5 minutes to set up |
| F21D4 | 0.3000 | 9.5 | Pellet was not wet and took less than 5 minutes to set up |
| F21D5 | 0.2727 | 10.4 | Pellet was not wet and took less than 5 minutes to set up |
| F21D6 | 0.2480 | 11.3 | Pellet was not wet and took less than 5 minutes to set up |
| F21D7 | 0.2250 | 12.3 | Pellet was not wet and took less than 5 minutes to set up |
| F21D8 | 0.2050 | 13.4 | Pellet was not wet and took less than 5 minutes to set up |

The pellets formed over a broad range of contained bonding solution. It is generally advantageous to use the minimum amount of bonding solution that still produces a strong pellet. On this basis, such pellet would certain about 8% or more of the bonding solution and the percentage of soy based protein would be about $8\% \times 0.05 = 0.4\%$ or more. A preferred range of the soy based protein is from about 0.40% to 0.67%.

PELLETIZATION OF AMMONIUM CARBAMATE WITH SODIUM CHLORIDE

The present inventor discovered that a solution of humic acid, prepared by dissolving 10% of Surtech L-101 in aqua ammonia, as previously described, bonds a broad range of combinations of ammonium carbamate and sodium chloride into pellets. One drop of this solution was added to the following weights of pulverized and mixed, ammonium carbamate and sodium chloride and the wetted masses were then rolled into pellets with the following results:

| 50% Ammonium Carbamate with 50% Sodium Chloride Bonded with an Aqua Ammonia Solution of Humic Acid | | | |
|---|---|---|---|
| EXAMPLE NO. | Grams of Crystal Mixture | Percent Bonding Solution | Remarks |
| G5D1 | 0.6800 | 6.4 | Not enough solution to bond the crystals into a pellet |
| G5D2 | 0.6180 | 7.0 | Pellet was set up and dried in about 2½ minutes |
| G5D3 | 0.5110 | 8.3 | Pellet set up and dried in about 3 minutes |
| G5D4 | 0.4220 | 9.9 | Pellet set up and dried in about 3 minutes |
| G5D5 | 0.3490 | 11.7 | Pellet set up and dried in about 3 minutes |
| G5D6 | 0.2880 | 13.9 | Pellet set up and dried in about 3 minutes |
| G5D7 | 0.2380 | 16.3 | Pellet set up and dried in about 4½ minutes and became too wet |

From these data, a preferred range for humic acid is from between about 0.21% to 0.49%.

In order to determine the upper limit on the amount of sodium chloride that can be bonded with a bonding solution containing humic acid dissolved in aqua ammonia, a mixture containing 10% ammonium carbamate and 90% sodium chloride was tested, and the following results were obtained:

10% Ammonium Carbamate with 90% Sodium Chloride Bonded with a Solution of Humic Acid in Aqua Ammonia

| EXAMPLE NO. | Grams of Crystal Mixture | Percent Bonding Solution | Remarks |
| --- | --- | --- | --- |
| G5D16 | 0.4220 | 9.9 | Not enough solution to bond the crystals into a pellet |
| G5D17 | 0.3840 | 10.8 | Pellet set up and dried in about 2 minutes |
| G5D18 | 0.2380 | 16.3 | Pellet set up and dried in about 2¼ minutes |

As the percentage of sodium chloride in the crystal mix was increased, additional bonding solution was required in order to form a pellet. Humic acid additions between about 0.32% to 0.49% allowed pelletization. In an attempt to determine the upper limit of sodium chloride that would pelletize with this bonding solution, a mixture of 95% salt with 5% ammonium carbamate was tested.

5% Ammonium Carbamate with 95% Sodium Chloride Bonded with a Solution of Humic Acid in Aqua Ammonia

| EXAMPLE NO. | Grams of Crystal Mixture | Percent Bonding Solution | Remarks |
| --- | --- | --- | --- |
| G6D1 | 0.3840 | 10.8 | Mixture would not pelletize even with additional bonding solution |

A bonding solution composed of humic acid dissolved in aqua ammonia, will bond compositions of ammonium carbamate and sodium chloride in the range of from about 10% to 100% ammonium carbamate and from about 0% to 90% salt. As described above, as the percentage of sodium chloride in the mixture is increased, a higher percentage of bonding solution is required to produce a pellet. The maximum amount of salt in the mixture that can be bonded is between about 90% to 95%. Furthermore, 100% ammonium carbamate can be pelletized with about 7% of the bonding solution, while a mixture containing 90% salt and 10% ammonium carbamate requires over 10% of the bonding solution.

It was also discovered that a solution comprising a soy based protein which was prepared by dissolving 5% of Surtech P-827 in aqua ammonia, as previously described, bonds all proportions of ammonium carbamate and salt into pellets. One drop of this solution was added to the following weights of pulverized and mixed ammonium carbamate and sodium chloride, and the wetted mass was then rolled into pellets with the following results.

50% Ammonium Carbamate with 50% Sodium Chloride Bonded with an Aqua Ammonia Solution of a Soy Based Protein

| EXAMPLE NO. | Grams of Crystal Mixture | Percent Bonding Solution | Remarks |
| --- | --- | --- | --- |
| G5D8 | 0.4000 | 7.3 | Pellet formed and dried in about 2½ minutes |
| G5D9 | 0.4400 | 6.7 | Pellet formed and dried in about 2¼ minutes |
| G5D10 | 0.4840 | 6.1 | Not enough solution to bond the crystals into a pellet |
| G5D11 | 0.3310 | 8.7 | Pellet formed and dried in about 6 minutes |
| G5D12 | 0.2740 | 10.3 | Pellet formed and dried in about 2 minutes |
| G5D13 | 0.2260 | 12.3 | Pellet formed and dried in about 2 minutes |
| G5D14 | 0.1870 | 14.5 | Pellet formed and dried in about 2 minutes |
| G5D15 | 0.1550 | 16.9 | Pellet formed and dried in about 4 minutes |

The soy based protein in aqua ammonia bonded the mixture of 50% ammonium carbamate and 50% sodium chloride so that it pelletized more readily than did either pure ammonium carbamate or the mixtures which contained 10% or less or ammonium carbamate. From these data, the preferred range for the soy based protein is from about 0.34% to 0.85%.

10% Ammonium Carbamate with 90% Sodium Chloride Bonded with an Aqua Ammonia Solution of a Soy Based Protein

| EXAMPLE NO. | Grams of Crystal Mixture | Percent Bonding Solution | Remarks |
| --- | --- | --- | --- |
| G5D19 | 0.2740 | 10.3 | Not enough solution to bond the crystals together |
| G5D20 | 0.2490 | 11.3 | Not enough solution to bond the crystals together |
| G5D21 | 0.2260 | 12.3 | Not enough solution to bond the crystals together |
| G5D22 | 0.2050 | 13.4 | Pellet formed and dried in about 2 minutes |
| G5D23 | 0.1860 | 14.5 | Pellet formed and dried in about 2 minutes |
| G5D24 | 0.1690 | 15.8 | Pellet formed and dried in about 1 minute |
| G5D25 | 0.1540 | 17.0 | Pellet formed and dried in about 1 minute |

This mixture of 10% ammonium carbamate with 90% sodium chloride pelletized surprisingly well. Significantly, more of the bonding solution comprising the soy based protein was required to pelletize the crystal mix. From the data, the preferred range of the soy based protein for this mixture is form about 0.67% to 0.85%.

5% Ammonium Carbamate with 95% Sodium Chloride Bonded with an Aqua Ammonia Solution of a Soy Based Protein

| EXAMPLE NO. | Grams of Crystal Mixture | Percent Bonding Solution | Remarks |
| --- | --- | --- | --- |
| G6D2 | 0.2050 | 13.4 | Pellet formed and dried in about 2 minutes |
| G6D3 | 0.2260 | 12.2 | Not enough solution to bond the crystals into a pellet |

-continued

5% Ammonium Carbamate with 95% Sodium Chloride Bonded
with an Aqua Ammonia Solution of a Soy Based Protein

| EXAMPLE NO. | Grams of Crystal Mixture | Percent Bonding Solution | Remarks |
|---|---|---|---|
| G6D4 | 0.1860 | 14.5 | Pellet formed and dried in about 2 minutes |
| G6D5 | 0.1690 | 15.8 | Pellet formed and dried in about 1 minute |
| G6D6 | 0.1540 | 17.0 | Pellet formed and dried in about 1 minute |

These test results were unexpected because the bonding solution made from humic acid would not bond a crystal mixture comprising only 5% ammonium carbamate. Accordingly, there was no expectation that the bonding solution made from the soy based protein would bond the same. After discovering that such bonding did in fact occur, the following tests related to bonding sodium chloride were conducted:

Sodium Chloride Bonded with an Aqua
Ammonia Solution and a Soy Based Protein

| EXAMPLE NO. | Grams of Crystal Mixture | Percent Bonding Solution | Remarks |
|---|---|---|---|
| G6D8 | 0.1540 | 17.0 | Not enough solution to bond the crystals into a pellet |
| G6D9 | 0.1400 | 18.4 | Pellet formed and dried in about 2 minutes |

A higher percentage of bonding solution, namely 18.4%, was required to bond sodium chloride into a pellet. This value corresponds to 0.92% of the soy based protein in the pellet.

Based on the above results, all compositions containing sodium chloride and or ammonium carbamate can be bonded with an aqua ammonia solution containing a soy based protein.

CRUSHING TESTS

Believing that the crystals needed to be crushed to form a strong pellet, the present inventor conducted additional compaction tests in the laboratory. In these tests, the crystals were ground in a mortar and pestle before being compacted. It was then discovered that by placing the pellets in plastic vials and storing them in a pressurized container, the pellets would, on standing, actually increase in strength as opposed to losing strength.

The need to keep the crystals in a pressure tight container was thus determined to be important for the purpose of producing pellets that would remain stable. Based on this finding, arrangements were made with two associated companies to crush the ammonium carbamate crystals and then to pelletize the crushed crystals in a pan granulator. Before running the crushing tests, there was a concern that, because of the softness of the crystals, the crushed crystals might blind the screen in a hammer mill. A second concern was that the crushing operation might cause overheating of the crystals.

Example A7C1 was conducted in a hammer mill with the hammers turning at 9750 rpm, and it was found that the product produced remained cool and that the screens did not become blinded. The product produced, however, was too fine to adequately feed into a pan granulator.

In Example A7C2, the openings in the screens were enlarged, first to 3/32 inch and then to 3/16 inch, yet the product produced was still too fine.

In Example A7C3, the screen openings were 3/16 inch, and 20% of the material being ground passed through a 200 mesh screen, and the speed of the hammers was reduced to 5900 rpm. The product which was produced was coarse enough to feed well into the pan granulator, and also fine enough to form a strong spherical pellet having a diameter of about ⅛ inch.

An adjustable pan granulator, such as a DP-14 Agglo-Miser 14 inch pan granulator, may be used in accordance with the present invention. The tilt and speed of the pan can be adjusted to allow crushed crystals to run down the face of the pan and to break from the outside circumference of the pan at a selected position.

Based on the above results, the hammer mill is an excellent device for crushing the ammonium carbamate crystals. During the crushing operation the crystals remained cool and the screens did not become blinded. By adjusting the screens on the hammer mill and the speed of the hammers, the product so produced was free flowing. Such a product can be fed into a pan granulator.

SUMMARY OF METHOD OF PRODUCTION OF PELLETS

The method described above may be summarized as comprising the following steps:
Producing ammonium carbamate in a solution;
crystallizing the ammonium carbamate from the solution;
separating the ammonium carbamate crystals from the solution;
washing the separated crystals with liquid ammonia to dry the crystals;
crushing the dried crystals;
agglomerating the crushed crystals; and
storing the agglomerated crystals.

A method of forming pellets of ammonium carbonate which are especially useful as a roadway deicer and may be delivered by standard spreading vehicles has been described above. It will be understood by those skilled in the art, however, that modifications may be made in the crushing and pelletizing steps to produce products having different characteristics.

DESCRIPTION OF A PILOT PLANT

Referring to FIG. 1, first absorber 10 is conventionally employed in a urea production plant as described above. In accordance with the present invention, the solution in the first absorber herein referred to as the "bottoms liquid", at a pressure of approximately 225 psi, is fed through pipe 11 under the control of valve 12 into a crystallization chamber 15 where the liquid pressure is reduced to and maintained at about 100 psig.

Conventional heat exchange elements (not shown) remove heat by way of liquid flowing through pipes 16 and 17.

The crystallized product is discharged through outlet 19 to diverter valve 20 and caused to flow through either of pipes 21 or 22 into one of pressure filters 23 or 24, which filters are maintained at a pressure below that of the crystallization chamber 15.

For drying the ammonium carbamate crystals, as described above, a liquid ammonia line 8, which is controlled by a diverter valve 9, alternately feeds ammonia liquid to the pressure filter at a pressure greater than the discharge pressure of the filter or the pressure at which the ammonia would become a gas. Filtrate from these filters is recirculated through lines 25 and 26 by pumps 27 and 28, and controlled by diverter valves 29 and 30 to the crystallization chamber 15. The diverter valves may be operated to cause the filtrate and any ammonia in the line to return to the first absorber 10 through lines 31, 32 such as, for example, during a shutdown of the crystallization chamber.

Crystals that are collected and dried in the pressure filters are discharged alternately through lines 34 and 35 to line 36 and to a hammer mill 38.

From the hammer mill 38, the crushed crystals are fed to a pan granulator 40 and then onto sizing screens 41. Undersize pellets pass through line 42 and to hammer mill 38. Pellets of selected size are transferred through line 44 to storage tank 45 for storage under a pressure sufficient to prevent volatilization of the ammonium carbamate.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims, and their equivalents.

What is claimed is:

1. A method comprising:
   providing a solution containing ammonium carbamate, water, ammonia and urea;
   cooling said solution to a temperature of from about 15° C. to about 30° C. while maintaining said solution at a pressure above about 50 psig; and
   crystallizing ammonium carbamate crystals from the cooled solution.

2. The method of claim 1, further comprising the step of separating the ammonium carbamate crystals from the solution.

3. The method of claim 2, wherein the step of separating comprises filtering the ammonium carbamate crystals.

4. The method of claim 2, further comprising the step of drying the ammonium carbamate crystals by washing the crystals with ammonia at a pressure at which the ammonia is substantially in a liquid state.

5. The method of claim 4, wherein the ammonium carbamate crystals are washed until their moisture content is less than approximately 5%.

6. The method of claim 4, wherein the liquid ammonia pressure is above approximately 20 psig.

7. The method of claim 4, further comprising the step of crushing the dried ammonium carbamate crystals to form a free-flowing powder.

8. The method of claim 7, wherein the crystals are crushed by a hammer mill.

9. The method of claim 7, further comprising the step of agglomerating the crushed ammonium carbamate crystals with a binding medium to form approximately spherical pellets.

10. The method of claim 9, wherein said binding medium comprises humic acid dissolved in aqua ammonia.

11. The method of 10, wherein said pellets comprise from about 0.21 to about 0.35 wt. % of said humic acid.

12. The method of claim 11 wherein said pellets comprise about 0.24 wt % of said humic acid.

13. The method of claim 9 wherein said binding medium comprises a soy based protein having a molecular weight of about 150,000 to 200,000 dissolved in aqua ammonia.

14. The method of claim 13, wherein said pellets comprise from about 0.40 to about 0.67 wt. % of said soy based protein.

15. The method of claim 14 wherein said pellets comprise about 0.40 wt. % of said soy based protein.

16. The method of claim 9, wherein the crushed crystals are agglomerated in a pan granulator.

17. The method of claim 9, wherein the pellets have a diameter of from approximately ⅛ in. to 174 in.

18. The method of claim 9, further comprising the step of storing the pellets in a closed vessel to contain the vapor of the ammonium carbamate at the storage temperature and the dissociation pressure of said vapor is from about 0.24 psig at 0° C. to 16 psig at 60° C.

19. The method of claim 1, wherein said solution is bottoms liquid from a urea plant. from about 0.40 to about 0.7 wt. % of said soy based protein.

20. A method comprising:
   providing a solution containing ammonium carbamate, water, ammonia and urea;
   cooling said solution to a temperature of from about 15° C. to about 30° C. while maintaining said solution at a pressure above about 50 psig;
   crystallizing ammonium carbamate crystals from the cooled solution;
   separating said ammonium carbamate crystals from said cooled solution; and
   agglomerating said ammonium carbamate crystals with a binding medium to form pellets.

21. The method of claim 20, wherein said binding medium comprises humic acid dissolved in aqua ammonia.

22. The method of 21, wherein said pellets comprise from about 0.21 to about 0.35 wt. % of said humic acid.

23. The method of claim 20, wherein said binding medium comprises a soy based protein having a molecular weight of about 150,000 to 200,000 dissolved in aqua ammonia.

24. The method of claim 23, wherein said pellets comprise from about 0.40 to about 0.67 wt. % of said soy based protein.

25. A pellet made according to the process of claim 21.

26. A pellet made according to the process of claim 23.

* * * * *